US010520485B2

(12) United States Patent
Laukkanen et al.

(10) Patent No.: US 10,520,485 B2
(45) Date of Patent: Dec. 31, 2019

(54) ANALYTICAL METHOD FOR DETERMINING THE CONCENTRATION OF OXIDIZED NANOFIBRILLAR CELLULOSE IN A SAMPLE

(71) Applicant: UPM-KYMMENE CORPORATION, Helsinki (FI)

(72) Inventors: Antti Laukkanen, Helsinki (FI); Jaakko Pere, Vantaa (FI); Atte Mikkelson, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 641 days.

(21) Appl. No.: 14/783,735

(22) PCT Filed: Apr. 11, 2014

(86) PCT No.: PCT/FI2014/050266
§ 371 (c)(1),
(2) Date: Oct. 9, 2015

(87) PCT Pub. No.: WO2014/167189
PCT Pub. Date: Oct. 16, 2014

(65) Prior Publication Data
US 2016/0299119 A1 Oct. 13, 2016

(30) Foreign Application Priority Data
Apr. 12, 2013 (FI) .................... 20135361

(51) Int. Cl.
G01N 33/34 (2006.01)
C12Q 1/40 (2006.01)
G01N 30/64 (2006.01)
G01N 30/72 (2006.01)
G01N 30/96 (2006.01)

(52) U.S. Cl.
CPC .............. *G01N 33/34* (2013.01); *C12Q 1/40* (2013.01); *C12Y 302/01* (2013.01); *C12Y 302/01004* (2013.01); *C12Y 302/01022* (2013.01); *C12Y 302/01025* (2013.01); *C12Y 302/01055* (2013.01); *G01N 30/64* (2013.01); *G01N 30/7233* (2013.01); *G01N 30/96* (2013.01); *G01N 2333/924* (2013.01); *G01N 2333/94* (2013.01); *G01N 2333/942* (2013.01)

(58) Field of Classification Search
CPC .. H04L 5/003; H04W 28/18; H04W 72/0446; C12Q 1/40; C12Y 302/01; C12Y 302/01004; C12Y 302/01022; C12Y 302/01025; C12Y 302/01055; D21H 11/18; D21H 11/20; G01N 2333/924; G01N 2333/94; G01N 2333/942; G01N 30/64; G01N 30/7233; G01N 30/96; G01N 33/34; G01N 33/343
See application file for complete search history.

(56) References Cited

U.S. PATENT DOCUMENTS 1,829,110 A   10/1931  Richter
6,048,707 A   4/2000   Klock, Jr.
2015/0267164 A1*  9/2015  Laukkanen ........ C12N 5/0062
                                        435/6.12

FOREIGN PATENT DOCUMENTS

WO    WO 88/10422 A1    12/1988
WO    WO 97/47764 A1    12/1997
WO    WO 2010/092239 A1  8/2010

OTHER PUBLICATIONS

Stelte et al. (2009) Ind. Eng. Chem. Res. 48: 11211-11219. (Year: 2009).*
Horn et al. (2012) Biotechnology for Biofuels 5: 1-12 (Year: 2012).*
Rohrer, J. Analysis of Carbohydrates by High-Performance Anion-Exchange Chromatography with Pulsed Amperometric Detection (HPAE-PAD) ThermoFisher Technical Note 20 (http://tools.thermofisher.com/content/sfs/brochures/TN-20-Analysis-Carbohydrates-HPAE-PAD-TN70671-EN.pdf) accessed Oct. 29, 2018 (Year: 2018).*
Cherian et al. (2011) Carbohydrate Polymers 86: 1790-1798. (Year: 2011).*
Association of the Nonwoven Fabrics Industry webpage "About Nonwovens". (http://www.inda.org/about-nonwovens/) accessed Sep. 19, 2019. (Year: 2019).*
Sequeira et al. (2010) Cellulose 17: 1147-1158. (Year: 2010).*
Besbes et al., "Nanofibrillated cellulose from TEMPO-oxidized eucalyptus fibres: Effect of the carboxyl content", Carbohydrate Polymers, vol. 84, Issue 3, Mar. 17, 2011, pp. 975-983.
Filson et al., "Characterization of sugars from model and enzyme-mediated pulp hydrolyzates using high-performance liquid chromatography coupled to evaporative light scattering detection", Bioresource Technology, vol. 100, 2009, pp. 6661-6664.
International Search Report issued in PCT/FI2014/050266, dated Jul. 31, 2014.

(Continued)

Primary Examiner — Lisa J Hobbs
(74) Attorney, Agent, or Firm — Nixon Peabody LLP

(57) ABSTRACT

The present invention provides a method for determining carbonyl ratio and/or concentration of oxidized nanofibrillar cellulose in a sample. In accordance with the invention oxidized nanofibrillar cellulose comprised in the sample is enzymatically hydrolyzed into oxidized cellobioses which are specific markers to oxidized nanofibrillar cellulose. The cellobioses may be then analyzed and quantified to reveal the amount of oxidized nanofibrillar cellulose in the sample. A method for determining the concentration of oxidized nanofibrillar cellulose in a sample comprises steps of providing an analytical sample of material comprising oxidized nanofibrillar cellulose; hydrolyzing the analytical sample to breakdown products of oxidized nanofibrillar cellulose in presence of one or more enzymes; subjecting the breakdown products to a separation analysis to reveal the relative amounts of the breakdown products; and determining the concentration of oxidized nanofibrillar cellu-lose.

16 Claims, 8 Drawing Sheets

(56) References Cited

OTHER PUBLICATIONS

Kim et al., "Enzymatic degradation of oxidized cellulose hydrogels", Polymer Degradation and Stability, vol. 95, Issue 12, Dec. 2010, pp. 2277-2280.
Search Report issued in Finnish Patent Application No. 20135361, dated Dec. 10, 2013.
Szengyel et al., "Effect of Acetic Acid and Furfural on Cellulase Production of Trichoderma reesei RUT C30", Applied Biochemistry and Biotechnology, vol. 89, 2000, pp. 31-42.
Written Opinion issued in PCT/FI2014/050266, dated Jul. 31, 2014.

\* cited by examiner

ANALYTICAL METHOD FOR DETERMINING THE CONCENTRATION OF OXIDIZED NANOFIBRILLAR CELLULOSE IN A SAMPLE

FIELD OF THE INVENTION

The present invention relates to a method for analyzing cellulosic samples, and more specifically to an analytical method suitable for use in determination of concentration and/or carbonyl ratio of oxidized nanofibrillar cellulose in a sample.

BACKGROUND OF THE INVENTION

Oxidized nanofibrillar cellulose is a cellulose derivative used as an additive in papermaking. The retention of the fibrils in the paper is difficult to determine due to lack of a reliable analytical method. Accordingly, there is a demand for an analytic method for the determination of the concentration of oxidized nanofibrillar cellulose and/or its carbonyl ratio in a material and thus the retention of oxidized nanofibrillar cellulose in the paper products.

BRIEF DESCRIPTION OF THE INVENTION

An object of the present invention is thus to provide a method to overcome the above problems and use of one or more enzymes for hydrolyzing a sample to its breakdown products in such a method. The objects of the invention are achieved by a method and use which are characterized by what is stated in the independent claims. The preferred embodiments of the invention are disclosed in the dependent claims.

BRIEF DESCRIPTION OF THE DRAWINGS

In the following the invention will be described in greater detail by means of preferred embodiments with reference to the attached drawings, in which FIG. 1 a schematic view of an apparatus for detecting and analyzing cellobiose and monosaccharide concentration of a sample after enzymatic hydrolysis.

DETAILED DESCRIPTION OF THE INVENTION

Figure 1:
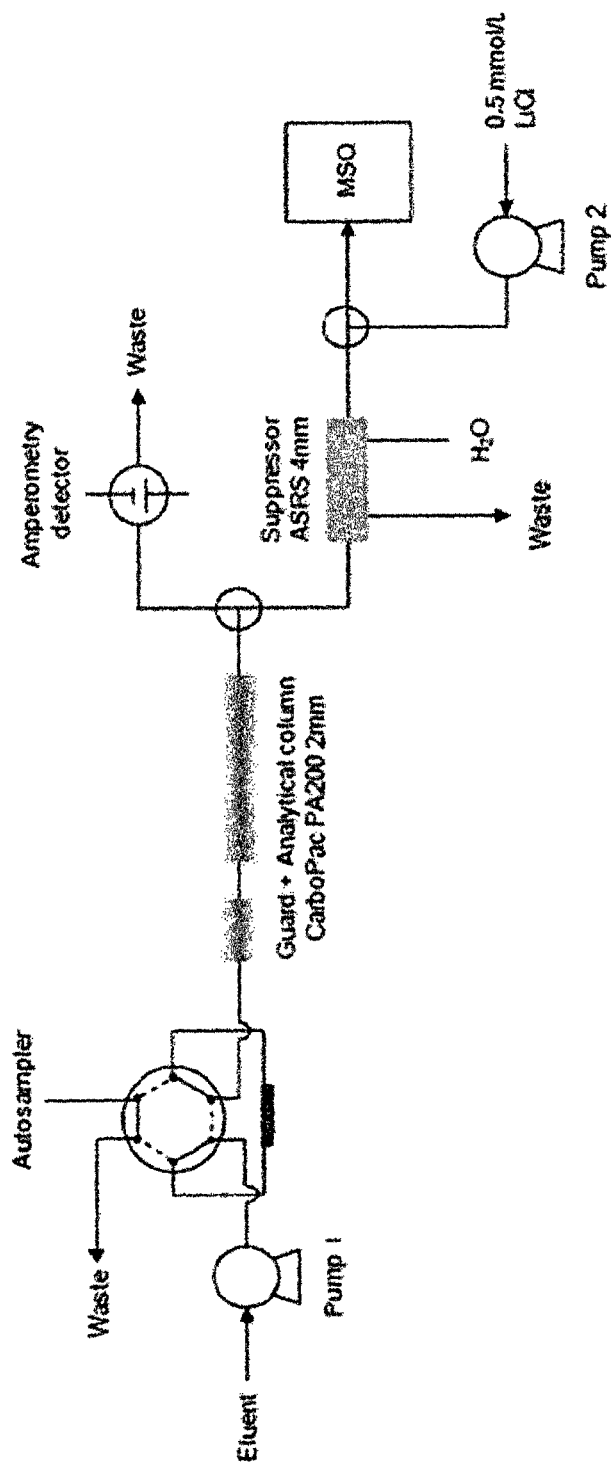

The present invention provides a method for determining concentration of oxidized nanofibrillar cellulose in a sample. In accordance with the invention oxidized nanofibrillar cellulose comprised in the sample is enzymatically hydrolyzed into oligosaccharides which may be then analyzed and quantified to reveal the amount of oxidized nanofibrillar cellulose in the sample. In the enzymatic hydrolysis dimeric oligohexoses, in particular oxidized cellobioses which are specific markers to oxidized nanofibrillar cellulose are formed and can be utilized to the quantification of oxidized nanofibrillar cellulose. The enzymatic hydrolysis will also hydrolyze any other cellulosic material present in the sample. Oxidized cellobiose markers, however, are typically not formed from the base pulp present in the sample. Cellulosic material, other than oxidized nanofibrillar cellulose, typically hydrolyses to monosaccharides and can thus be analyzed and identified separately from the oxidized cellobioses.

The term "nanofibrillar cellulose (NFC)" refers to isolated cellulose fibers and fiber bundles having a diameter in the submicron range. The length of the nanofibrillar cellulose may exceed one micrometer while the number-average fiber diameter is typically below 500 nm. The length of nanofibrillar cellulose is somewhat challenging to measure accurately, but rough estimates for length of native grade is from 1 to 100 micrometer, preferably from 1 to 50, and most preferably from 5 to 20 micrometers. The dimensions of the fibers and fiber bundles are dependent on raw material and disintegration method.

The celluloses utilized in NFC may be obtained from any cellulose raw material based on any plant material that contains cellulose, any microbial cellulose, or any cellulose raw material source that can be used in production of cellulose pulp, refined pulp, and NFC.

Plant material may be any wood derived or non-wood derived plant material. Said wood may be selected from softwood (SW) trees, such as spruce, pine, fir, larch, douglas-fir and hemlock, from hardwood (HW) trees, such as birch, aspen, poplar, alder, eucalyptus and acacia, and from mixtures of softwoods and hardwoods. Said non-wood plant material may be selected from agricultural residues, grasses and other plant materials, such as straw, leaves, bark, seeds, hulls, flowers, vegetables and fruits, from cotton, corn, wheat, oat, rye, barley, rice, flax, hemp, manilla hemp, sisal hemp, jute, ramie, kenaf, bagasse, bamboo and reed.

The cellulose raw material may also be derived from cellulose-producing micro-organisms, such as materials obtained from bacterial fermentation processes. The micro-organisms may be selected from the genus *Acetobacter, Agrobacterium, Rhizobium, Pseudomonas* and *Alcaligenes*, suitably the genus *Acetobacter* and particularly suitably the species *Acetobacter xylinum* or *Acetobacter pasteurianus*. Cellulose may also be obtained from algae, for example cellulose can be found in structural walls of green algae, brown algae, most of the red algae and most of the golden algae.

The term "cellulose pulp" refers to cellulose fibers, which are isolated from any cellulose raw material, using chemical, mechanical, thermo-mechanical, or chemi-thermo-mechanical pulping processes. Particularly cellulose pulp, which can be pulp of plant origin, especially wood (SW or HW pulp, for example bleached birch pulp) and where the cellulose molecules are oxidized, is easy to disintegrate to NFC.

NFC with desired properties and dimensions may be obtained by mechanical disintegration of cellulose pulp, oxidized cellulose raw material, microbial cellulose etc. is carried out with suitable equipment, such as a refiner, grinder, homogenizer, colloider, friction grinder, ultrasound-sonicator, fluidizer such as microfluidizer, macrofluidizer or fluidizer-type homogenizer. Thus NFC refers to mechanically disintegrated products. Several different grades (types) of NFCs have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final NFC product. Typically, native or non-derivatized grades have larger diameters and wider fibril size distribution while the derivatized grades have smaller diameters and narrower size distributions.

The term "oxidized nanofibrillar cellulose" refers to NFC where at least some of the C6 primary hydroxyl groups of cellulose are selectively oxidized to carbonyl groups, i.e. aldehydes and/or carboxyl groups. The oxidation may be accomplished for example catalytically by a heterocyclic nitroxyl compound, for example 2,2,6,6-tetramethylpiperidinyl-1-oxyl free radical (TEMPO). The degree of carbonyl substitution i.e. the carbonyl content of in the oxidized nanofibrillar cellulose is typically from 300 to 1800 µmol/g, preferably from 600 to 1550 µmol/g, more preferably from 750 to 1050 µmol/g. The carboxylic acid content of the oxidized nanofibrillar cellulose is typically from 300 to 1500 µmol/g, preferably from 600 to 1200 µmol/g, more preferably from 750 to 850 µmol/g. The aldehyde group content of the oxidized nanofibrillar cellulose is typically from 1 to 300 µmol/g, preferably from 80 to 250 µmol/g, more preferably from 100 to 200 µmol/g. Typical dosages of oxidized NFC in pulp furnish are from 0.1 to 5% w/w, preferably from 0.5 to 2% w/w.

The oxidized NFC may have been pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. The oxidized NFC obtained from pretreated cellulose raw material contains sodium counter ion at C6 carbonyl group.

The number average diameter of oxidized nanofibrillar cellulose or nanofibrillar cellulose bundles may range from 1 to 500 nm, preferably from 2 to 200 nm, more preferably from 2 to 100 nm, most preferably from 2 to 20 nm. The length of oxidized NFC varies from 0.3 to 50 micrometers, preferably from 0.3 to 20 micrometers, and most preferably from 0.5 to 10 micrometers. All the information regarding sizes may be determined from electron microscopy images. The term "oxidized cellobiose" as used herein and hereafter refers to dimeric glucose compounds where the hydroxyl group at the C6-position of at least one of the glucose units has been selectively oxidized to a carbonyl group i.e. aldehyde or carboxyl group. Thus oxidized cellobiose may be a dimeric glucose compound comprising an aldehyde in C6 position of one of the glucose units or a dimer of glucose and glucuronic acid. In an aspect of the invention oxidized cellobiose is GlcA(b1-4)Glc (GlcAGlc) and/or Glc(b1-4)GlcA (GlcGlcA) and/or Glc(C6-aldehyde)(b1-4)Glc (Glc(C6-aldehyde)Glc) and/or Glc(b1-4)Glc(C6-aldehyde) (GlcGlc(C6-aldehyde)). The oxidized cellobioses are obtained by hydrolyzing the oxidized nanofibrillar cellulose in suitable conditions in accordance with the method of the present invention as discussed herein. The oxidized nanofibrillar cellulose may also hydrolyze to minor amounts of Glc(C6-aldehyde)GlcA, GlcAGlc(C6-aldehyde), GlcAGlcA and/or GlcA.

The method of the present invention is applicable for analyzing any samples comprising oxidized nanofibrillar cellulose in the sample matrix and allowing enzymatic hydrolysis to be accomplished. However, samples that contain inactivating components to enzymatic hydrolysis cannot be analyzed. Examples of sample materials comprising oxidized nanofibrillar cellulose include paper, cardboard, pulp, pulping liquor, cellulose based nonwovens, and aqueous solutions. In an aspect of the invention the sample material is pulp or paper.

Examples of suitable paper materials include the following paper grades. Base papers for self-adhesive labels, wherein furnish consists of a mixture of softwood and hardwood chemical pulp with optional filler and pigment coating. Glassine type papers have no filler and are highly transparent. For coated and filler containing release papers typical pigments are calcium carbonate and kaolin. These papers can be pigment coated from one side only and typical amount of coat weight is 5 to 10 $g/m^2$. Basis weight range of base papers is typically 45 to 65 $g/m^2$. Mechanical printing papers such as SC (super calandered) and LWC (light weight coated), wherein furnish is typically a mixture of mechanical pulp such as groundwood (GW), pressure groundwood (PGW) or TMP (thermomechanical pulp), chemical softwood pulp and possibly recycled fibre. Typical fillers for these grades are kaolin, calcium carbonate and talcum. Filler content of papers vary typically 5 to 35% and in case of coated grades, coat amount varies 5 to 15 $g/m^2$. Typical basis weight range for these papers is 40 to 70 $g/m^2$. Wood free paper consists of chemical soft and hard wood pulp. In some cases a small amount of mechanical pulp such as CTMP may be used as well. Typical filler for wood free paper is calcium carbonate and in case of wood free coated papers also kaolin may be present. Filler content of uncoated wood free papers vary typically in range of 15 to 35%. In case of coated wood free papers, pigment amount may be over 50% of total mass of paper. Basis weight range of wood free papers varies depending on the possible coat weight from 40 to 350 $g/m^2$. The method of the invention is particularly suitable for paper grades containing chemical and mechanical pulps and/or consisting of pulp produced from birch, pine and spruce.

In alternative aspect of the invention the sample material an aqueous solution for example pulp or paper machine circulation water for example wire water. Circulation waters of paper machine typically consist of fibers, fines, fillers, pigments and different process additives. Some examples of additives are starch, fixatives, alum, sizing agents and retention chemicals. Consistency of circulation water is typically less than 1%. Furthermore, the method of the present invention is suitable for determining migration of oxidized nanofibrillar cellulose from a material by analyzing washing solution obtained from washing the material and determining the amount of oxidized nanofibrillar cellulose in the washing solution.

The method of the present invention is particularly suitable for analyzing samples where the concentration of oxidized nanofibrillar cellulose is low, above 0.001% w/w, preferably between 0.01 to 5% w/w, more preferably between 0.1 to 1% w/w. The method for the present invention is further suitable for analyzing samples wherein the oxidized NFC is mixed with other cellulose containing material in solid state, in particular paper and board structure. Furthermore, the method of the present invention provides detailed analysis of the internal structure of the oxidized nanofibrillar cellulose, i.e. aldehyde vs. carboxylic acid ratio, which may be vital information for manufacturing process development.

In accordance with the present invention a method for determining the concentration of oxidized nanofibrillar cellulose in a sample comprises the steps of: (a) providing an analytical sample of material comprising oxidized nanofibrillar cellulose; (b) hydrolyzing the analytical sample to breakdown products of oxidized nanofibrillar cellulose in presence of one or more enzymes; (c) subjecting the breakdown products to a separation analysis to reveal the relative amounts of the breakdown products; and (d) determining the carbonyl ratio and/or concentration of oxidized nanofibrillar cellulose.

In one aspect of the present invention step (a) of the method comprises treating material comprising oxidized nanofibrillar cellulose to obtain a homogenous analytical sample of the material comprising oxidized nanofibrillar cellulose. The sample material can be treated by cutting it to small pieces, tearing apart, mixing, grinding, ball milling, sonication or refining to obtain a homogenous and representative sample of the material comprising oxidized nanofibrillar cellulose. The sample material is preferably suspended into water.

The enzymatic hydrolysis of the cellulosic material of the sample in step (b) can be accomplished utilizing a specific combination enzymes that are able to hydrolyzed b1→4 bonds in cellulose. It is commonly known that cellulases are able to hydrolyze b1→4 bonds in cellulose. For example endo-1,4-pglucanases (EGs) target cellulose chains in random locations away from the chain ends; exoglucanases or exocellobiohydrolases (CBHs) degrade cellulose by splitting off molecules from both ends of the chain producing cellobiose dimers; and [beta]-glucosidases (BGLs) hydrolyze the oligosaccharides produced and cellobiose units (produced during EG and CBH attack) to glucose. Respectively, NFC can be enzymatically hydrolyzed to corresponding breakdown products with an aid of cellulases. Total hydrolysis of NFC to monomeric sugars necessitates that the enzyme mixture contains also endo acting hemicellulases, such as xylanases, mannanases, β-D-glycosidases, β-D-xylosidases and β-D-mannosidases. When only partial hydrolysis is aimed composition of the enzyme mixture can be tuned to include excess endoglucanases and less or no cellobiohydrolases. In the latter case hemicellulases can be included into the mixture since they enhance hydrolytic action of cellulases.

The required enzyme mixture may be dependent of the nature of the analyzed sample. In an aspect of the present invention the enzymes in step (b) of the method are selected from the group consisting of cellulases and hemicellulases, more preferably from the group consisting of endoglucanases, cellobiohydrolases, xylanases, mannanases, β-D-glycosidases, β-D-xylosidases and β-D-mannosidases. For materials containing pectin the enzyme mixture of step (b) can also comprise pectinases in order to ease the decomposition of cellulosic material to oligosaccharides. In an aspect of the invention the activities of the enzyme mixture is preferably 50 FPU/g mixed cellulases; 5000 to 10 000 nkat/g endoglycanases (cellulases, xylanases, mannanases); 100 to 500 nkat/g α-arabinosidase, α-galactosidase, β-mannosidase; and 50 to 200 nkat/g β-xylosidase.

The enzymatic hydrolysis of the sample can be conducted with different enzymes at different environments. In an aspect of the invention the enzymatic hydrolysis is carried out at temperatures from 15 to 80° C., preferably from room temperature to 50° C., more preferably from 35 to 45° C. In a further aspect of the invention the invention the enzymatic hydrolysis is carried out at pH 3 to 8, preferably from 4 to 7. The hydrolysis time is suitably from 1 to 72 h, preferably from 3 to 48 h, more preferably from 12 to 24 h.

Step (c) can be practiced by subjecting the enzymatically hydrolyzed sample to analytical chromatography and detecting separated oxidized cellobioses and monosaccharides as a result of the analytical chromatography. Particularly advantageous techniques include high-performance liquid chromatography (HPLC) and high-performance anion exchange chromatography (HPAEC) coupled with a suitable detector for detecting the separated carbohydrates via specific interactions between the hydroxyl groups of the carbohydrates and the stationary phase of the column, although other techniques can be utilized. Suitable detectors include for example PAD, MS, RI and UV. In an aspect of the invention the anion exchange chromatography is HPAEC-PAD, HPAEC-MS or HPAEC-PAD-MSQ. The use of HPAEC allows selective separation of closely related cellobioses.

The anion exchange column utilized in the analytical separation of the carbohydrates resulting from the enzymatic hydrolysis of the oxidized NFC should be selected in such way that the oxidized cellobioses that are specific markers of the oxidized NFC are selectively separated from other carbohydrates and from each other. Any anion exchange columns known by the person skilled in the art to be suitable for separation of oxidized cellobioses can be utilized in the method of the invention.

Most commonly used five different types of separation modes/column categories that can be utilized for analyzing carbohydrates (monosaccharide, disaccharides, or longer oligosaccharides) are following. First category of columns utilizes hydrophilic Interaction. These columns include amino-binded silica gel columns with acetonitrile-water mobile phase and polyamine-bonded gel columns. Second category of columns utilizes ligand exchange. These columns comprise acidic cation-exchange resins with metal counter ions such as' $Ag^+$, $Ca^{2+}$ and/or $Pb^+$. These counter ions are commonly used with acidic cation-exchange resin for separating different kind of mono- and oligosaccharides.

Third category is borate complex anion exchange. In this technique carbohydrate-borate complexes are separated on an anion-exchange resin. Fourth category of columns is based on size exclusion. The separation of carbohydrates is depending on their size. Fifth category of columns utilizes anion-exchange. Anion-exchange technique uses quaternary ammonium (pellicular) resins under alkaline conditions. These columns provide excellent resolution for mono-, di- and oligosaccharides. Examples of such columns include CarboPac PA200, CarboPac PA100 and CarboPac PA1 (all manufactured by Dionex). In addition of these also other separation techniques/columns can be utilized.

In an aspect of the invention the anion exchange column is CarboPac PA200. For obtaining suitable separation anion exchange chromatography of oligosaccharides is typically performed using alkaline solution as a gradient.

Figure 2:
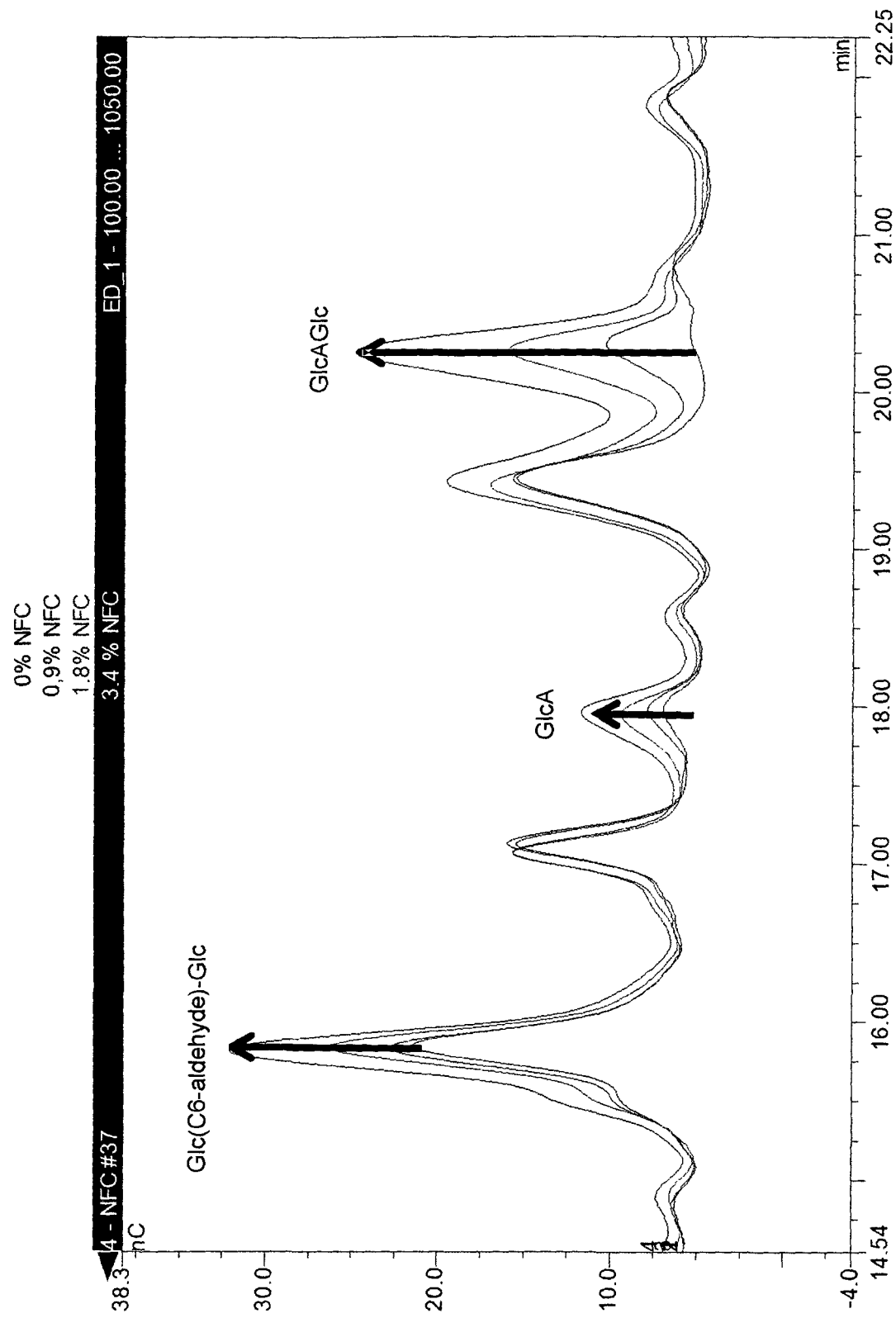
FIG. 2 is a graphical presentation of results achieved from HPAEC-PAD analysis of TEMPO oxidized birch pulp.
Figure 3:
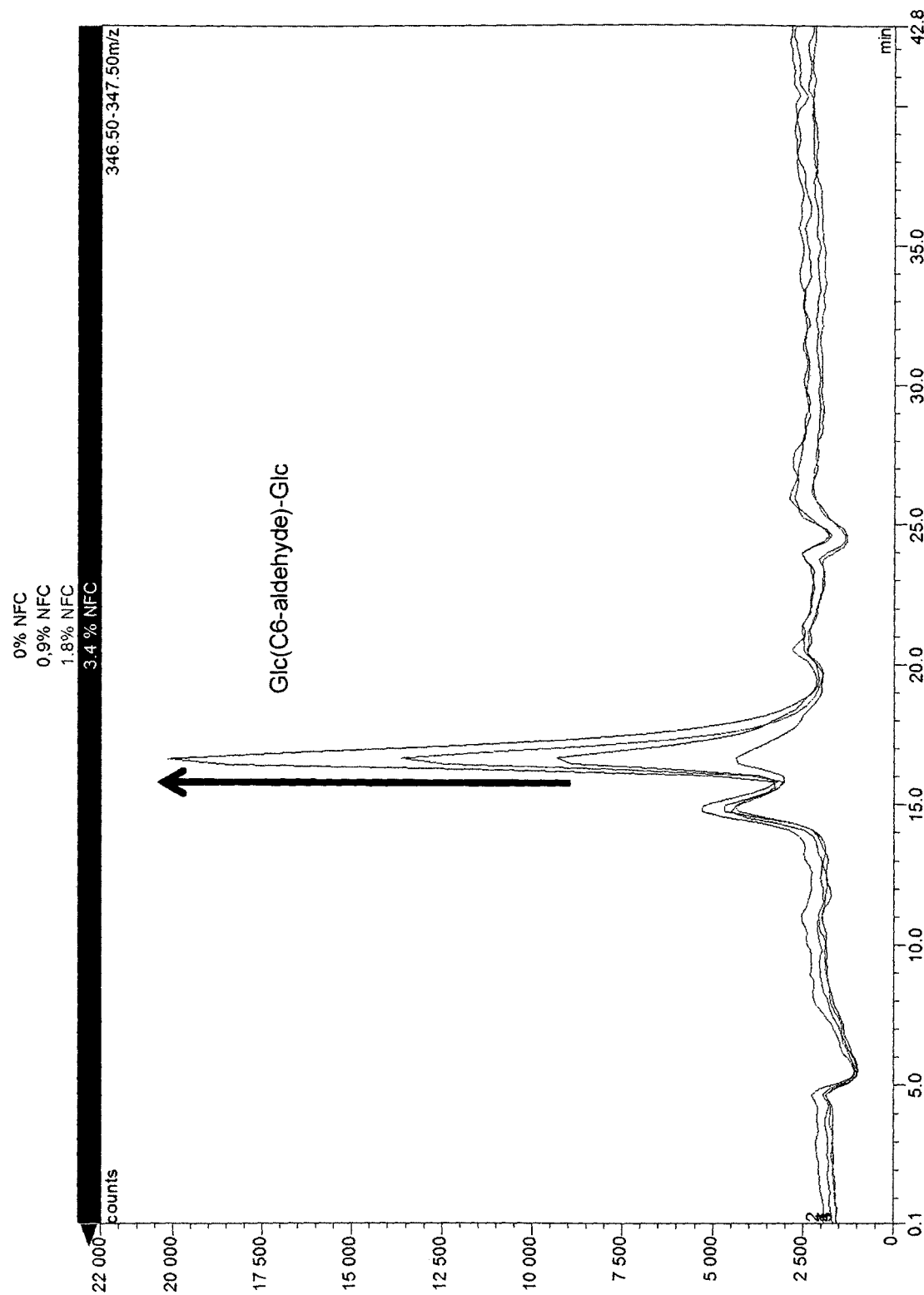
FIG. 3 is a graphical presentation of results achieved from HPAEC-MSQ analysis of TEMPO oxidized birch pulp.
Figure 4:
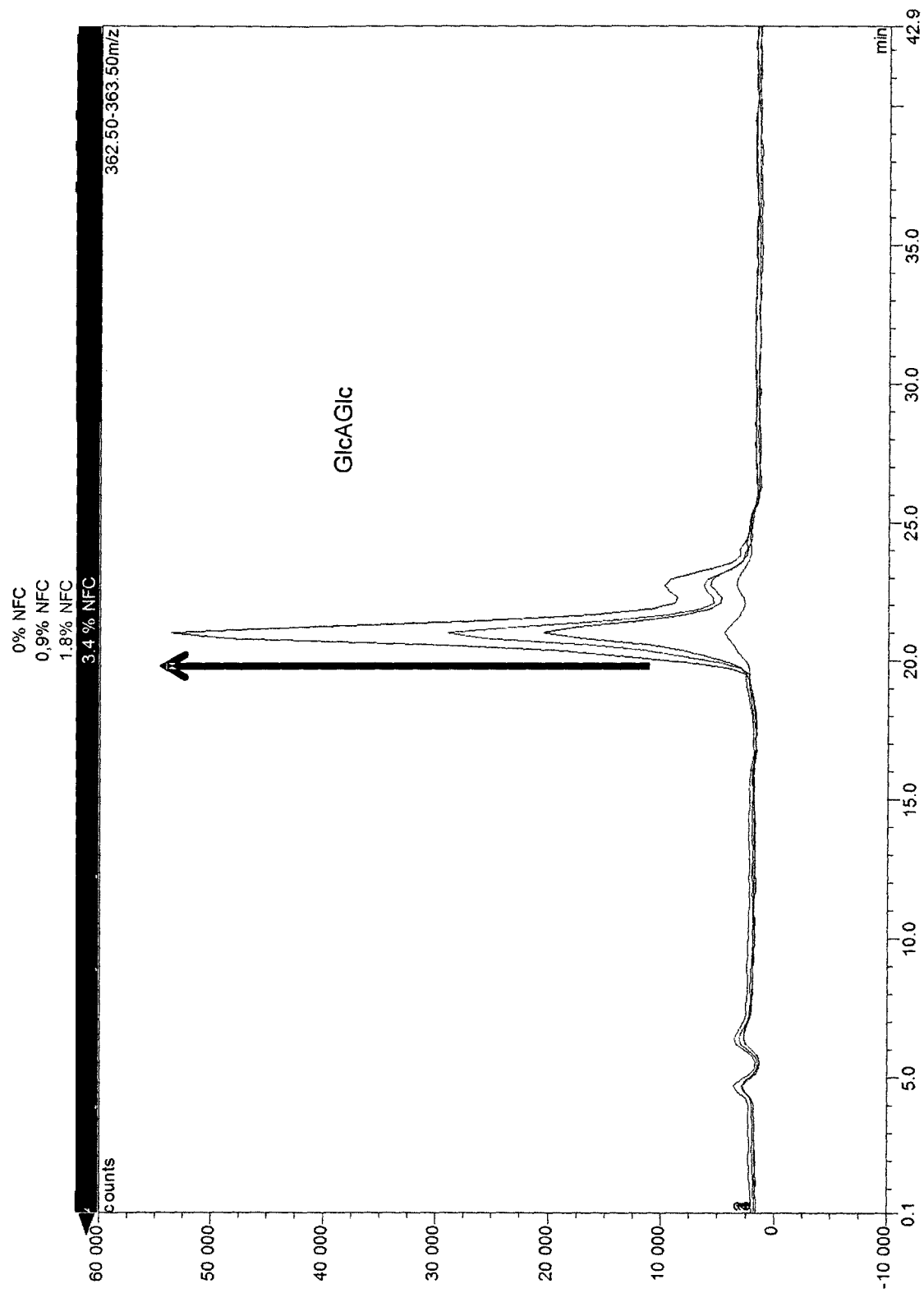
FIG. 4 is a graphical presentation of results achieved from HPAEC-MSQ analysis of TEMPO oxidized birch pulp.

FIG. 1 illustrates an analysis apparatus suitable for use in the method of the present invention comprising an analytical anion exchange column associated with a pulsed amperometry detector (PAD) and a single quadrupole mass spectrometer (MSQ). FIGS. 2, 3 and 4 illustrate typical chromatograms of enzymatically hydrolyzed samples of oxidized NFC comprising material. FIG. 2 is from a PAD detector when a series of exemplary samples of TEMPO oxidized birch pulp with different levels of oxidation were analyzed utilizing high performance anion exchange chromatography (HPAEC), while FIGS. 3 and 4 are from the same series of birch pulp samples utilizing MSQ detection. Utilizing the analytical information provided by the chromatograms the original amount of oxidized nanofibrillar cellulose in a sample can be quantified and the carbonyl ratio of oxidized nanofibrillar can be determined by calculation and comparison to standard samples.

In step (d) the concentration of oxidized nanofibrillar cellulose is advantageously determined by comparing the relative amounts of oxidized cellobioses in the analytical sample to standard samples. Preferably step (d) comprises determining aldehyde and carboxylic acid ratio of the oxidized nanofibrillar cellulose by comparing the relative amounts of GlcA(b1-4)Glc, Glc(b1-4)GlcA, Glc(C6-aldehyde)(b1-4)Glc and/or Glc(b1-4)Glc(C6-aldehyde). Alternatively or in addition the concentration of oxidized nanofibrillar cellulose may be determined by comparing the relative amounts of oxidized cellobioses to an internal standard.

The amount, i.e. concentration, of NFC can be determined by comparing the peaks of oxidized cellobioses of the analyzed sample with the corresponding peaks resulting from standard samples containing increasing amounts of NFC and which are enzymatically hydrolyzed and analyzed using the same techniques and conditions as the analyzed sample. For more reliable results the information obtained from the standard samples can be utilized to form a calibration curve to which the analyzed sample is the compared to. For obtaining reliable results the sample should be compared to at least two standard samples comprising different predetermined amounts of oxidized nanofibrillar cellulose.

For example marker "GlcGlcA" or "Glc(C6-aldehyde) Glc" area can be correlated to %—amount of oxidized nanofibrillar cellulose in the standard mixtures, since GlcGlcA and "Glc(C6-aldehyde)Glc" do not naturally occur in pulps or paper products. Integration of these markers in mixtures gives a good linearity to prepared standards. In the analysis of unknown samples, standard mixtures need to be treated and hydrolyzed similarly as the samples.

The present invention further provides use of one or more enzymes for hydrolyzing a sample to its breakdown products in a method of determining concentration of oxidized nanofibrillar cellulose in the sample.

In a particular embodiment of the present invention the concentration of oxidized nanofibrillar cellulose in the sample is determined by the method of the present invention. The used enzymes are advantageously selected from cellulases and hemicellulases, preferably from the group consisting of endoglucanases, cellobiohydrolases, xylanases, mannanases, β-D-glycosidases, β-D-xylosidases and β-D-mannosidases. In a further embodiment of the invention the enzymes further comprise pectinases.

The obtained hydrolyzed sample is preferably subjected to an anion exchange column suitable for selective separation of the oxidized cellobioses that are specific markers of the oxidized NFC from other carbohydrates and from each other as discussed above.

EXAMPLES

Example 1. Composition of Analyzed Materials

Two types of oxidized nanofibrillar cellulose were used in the studies.

Grade A:
fiber diameter, 2-6 nm
fiber length, 500-10000 nm
carboxylic acid content 800 μmol/g
aldehyde group content 100 μmol/g Grade B:
fiber diameter, 2-6 nm
fiber length, 500-10000 nm
carboxylic acid content 1000 μmol/g
aldehyde group content 100 μmol/g Preparation of Laboratory Sheets:

Pulp components were selected according to the paper grade produced. Pulp components were beaten and mixed prior to starch addition to furnish. Starch mixing time was 15 minutes. Oxidized nanofibrillar cellulose was added to the furnish after starch and mixing time was 5 minutes. Thereafter sheet making was started. Hand sheets were prepared using circulation water according to standard SCAN-CM 64:00. Number of buildup sheets was 12 instead of 8 buildup sheets according to the standard. Glassine type paper was produced in laboratory. Furnish used was a mixture of beaten chemical pine pulp and beaten chemical birch pulp. Pine and birch pulp mixing ratio was 30/70. Cationic starch addition amount to sheets was 1%. Pine and birch pulps were beaten separately and mixed thereafter together. Cationic starch was added to the furnish and the furnish was then mixed for 15 minutes. Oxidized nanofibrillar cellulose was added to the furnish and after 5 minutes mixing time sheet making was started. Hand sheets were prepared using circulation water according to standard SCAN-CM 64:00. Basis weight of hand sheets was 60 g/m2.

Paper Sample A:

Filler containing wood free paper was produced on a (pilot) paper machine. A mixture of beaten chemical pulp was used as raw material. Pine share was 25 to 30% w/w of fibers and birch share was 70 to 75% w/w of fibers. Cationic starch addition was 1 to 2% w/w. Calcium carbonate $CaCO_3$ was used as filler and filler content of samples varied between 20 to 25% w/w. Oxidized nanofibrillar cellulose dosage amount was varied between 0.5 to 2% w/w. Basis weight of paper produced was around 70 g/m$^2$.

Paper Sample B:

Filler containing LWC base paper was produced on a (pilot) paper machine. A mixture of beaten chemical pine pulp and mechanical pulp was used as raw material. Pine share was 30% w/w of fibers and mechanical pulp share was 70% w/w of fibers. Cationic starch addition was 1 to 2% w/w. China clay was used as filler and filler content of samples varied between 6 to 8% w/w. Oxidized nanofibrillar cellulose dosage amount was varied between 1 to 3% w/w. Basis weight of paper produced was around 38 g/m$^2$.

Paper Sample C:

Filler containing LWC base paper was produced on a paper machine. A mixture of beaten chemical pine pulps was used as raw material. Pine share was 40% w/w of fibers and mechanical pulp share was 60% w/w of fibers. Cationic starch addition was 0.3% w/w. No filler was used. Oxidized nanofibrillar cellulose dosage amount was varied between 1 to 3% w/w. Basis weight of paper produced was around 35 g/m$^2$.

Example 2. Composition of the Enzyme Mixture and Description of Enzymatic Hydrolysis The enzyme mixture was prepared of commercial enzymes, including cellulases, xylanases and mannanases. When appropriate, some side activities were added from commercial sources in order to ascertain high enough concentration of all necessary activities. The mixture was buffered in Na-acetate buffer, pH 5. Disturbing components (e.g. sugars, stabilizers) originating from commercial preparations were removed by gel filtration with Biogel P-6 (Bio-Rad) gel.

Sufficient activities in dosing of the mixture are the following: 50 FPU/g mixed cellulases; 5000-10000 nkat/g endoglycanases (cellulases, xylanases, mannanases); 100-500 nkat/g α-arabinosidase, α-galactosidase, β-mannosidase; 50-200 nkat/g β-xylosidase.

For the hydrolysis 100-250 mg of sample (calculated as dry weight) was weighed into a 50 ml vial (in duplicates). The volume of the added enzyme mixture was calculated, based on a nominal dosage of 50 FPU/g, using the equation:

$$\text{Amount of enzyme mixture (ml)} = \frac{50 \; FPU/g \times \text{sample dry weight (g)}}{\text{Activity of the enzyme mixture } (FPU/\text{ml})}$$

The consistency of the hydrolysis mixture was fixed to 1.6% with 0.1 M Na-acetate buffer pH 5. The tubes were incubated at +40° C. under mixing for 48 hours. After hydrolysis the sample was centrifuged (e.g. 3200 rpm/10 min) and the supernatant was separated and incubated in boiling water for 10 min in order to inactivate enzymes. The sediment (precipitated enzymes) was removed by centrifugation and the clear supernatant was used for HPLC analysis.

Example 3. Identification of the Markers for Oxidized Nanofibrillar Cellulose

The quantitative analysis of oxidized NFC was carried out by high performance anion exchange chromatography (HPAEC-PAD) using a CarboPac PA-200 column at 30° C. (DionexCorp, USA) in a Dionex ICS-3000 series chromatograph equipped with pulse amperometric detection (PAD). Alkaline gradient was used for the determination of carbohydrates with a flow rate of 0.3 ml/min. HPAEC-MSQ detection was used to verify and to identify unidentified compound as Li-adducts $[M+Li]^+$ at $[M+7]^+$ in the positive mode.

Figure 5:
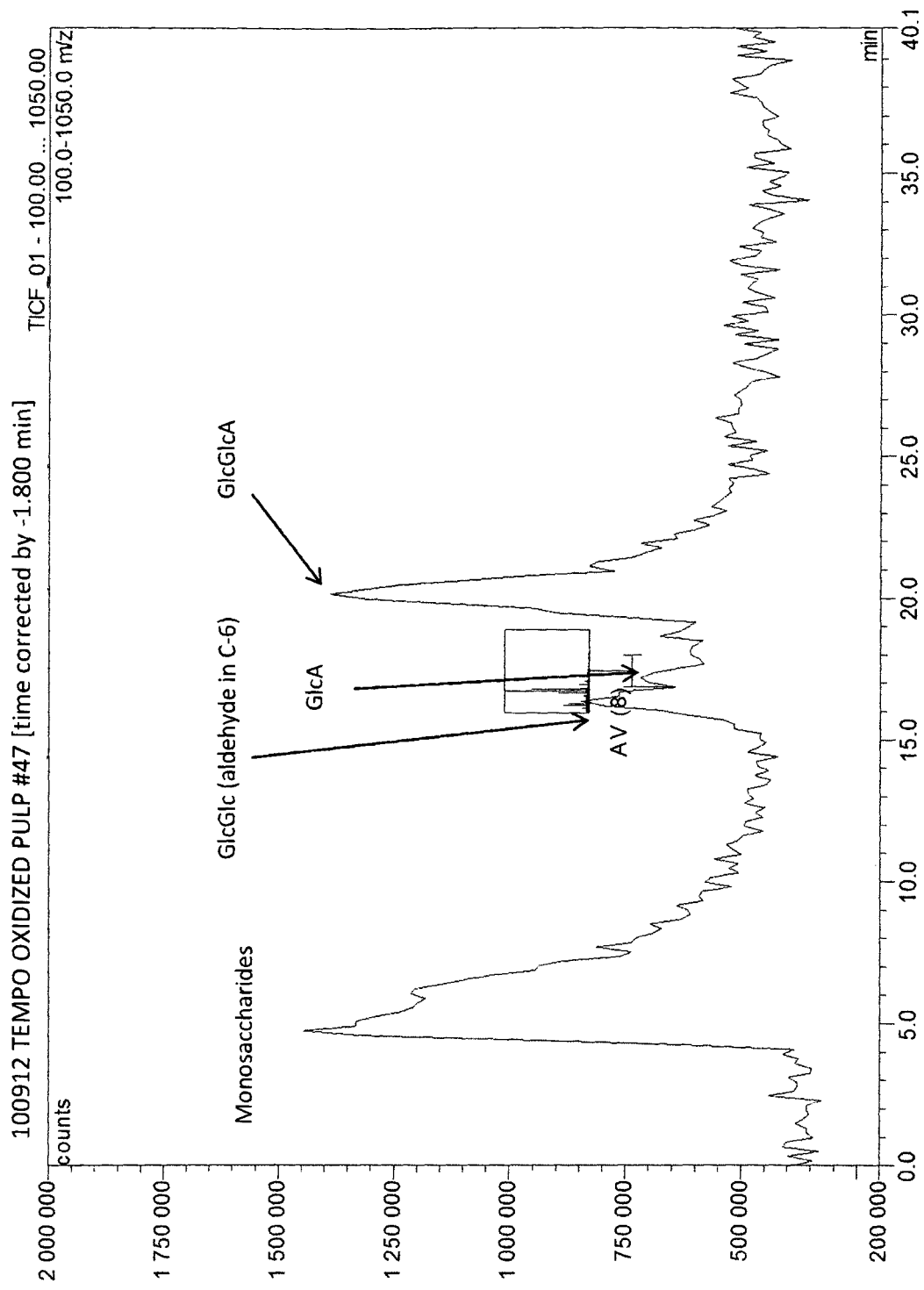
FIG. 5 is a MSQ-chromatogram of oxidized starting material which is used to prepare standard.

Measured TIC chromatogram (total ion chromatogram) from pure oxidized nanofibrillar cellulose was used to identify oxidized compounds using scan mode and scan range of 100-1050 m/z (FIG. 5). It was shown that enzymatic hydrolysis of oxidized nanofibrillar cellulose resulted to mainly dimeric breakdown products, i.e. oxidized cellobioses, and glucuronic acid in addition to monomeric sugars, mainly glucose and xylose. Theoretical molecular mass values of dimeric oxidized carbohydrates as lithium adducts were compared to measured ones. GlcA was identified using a commercial standard.

Figure 6:
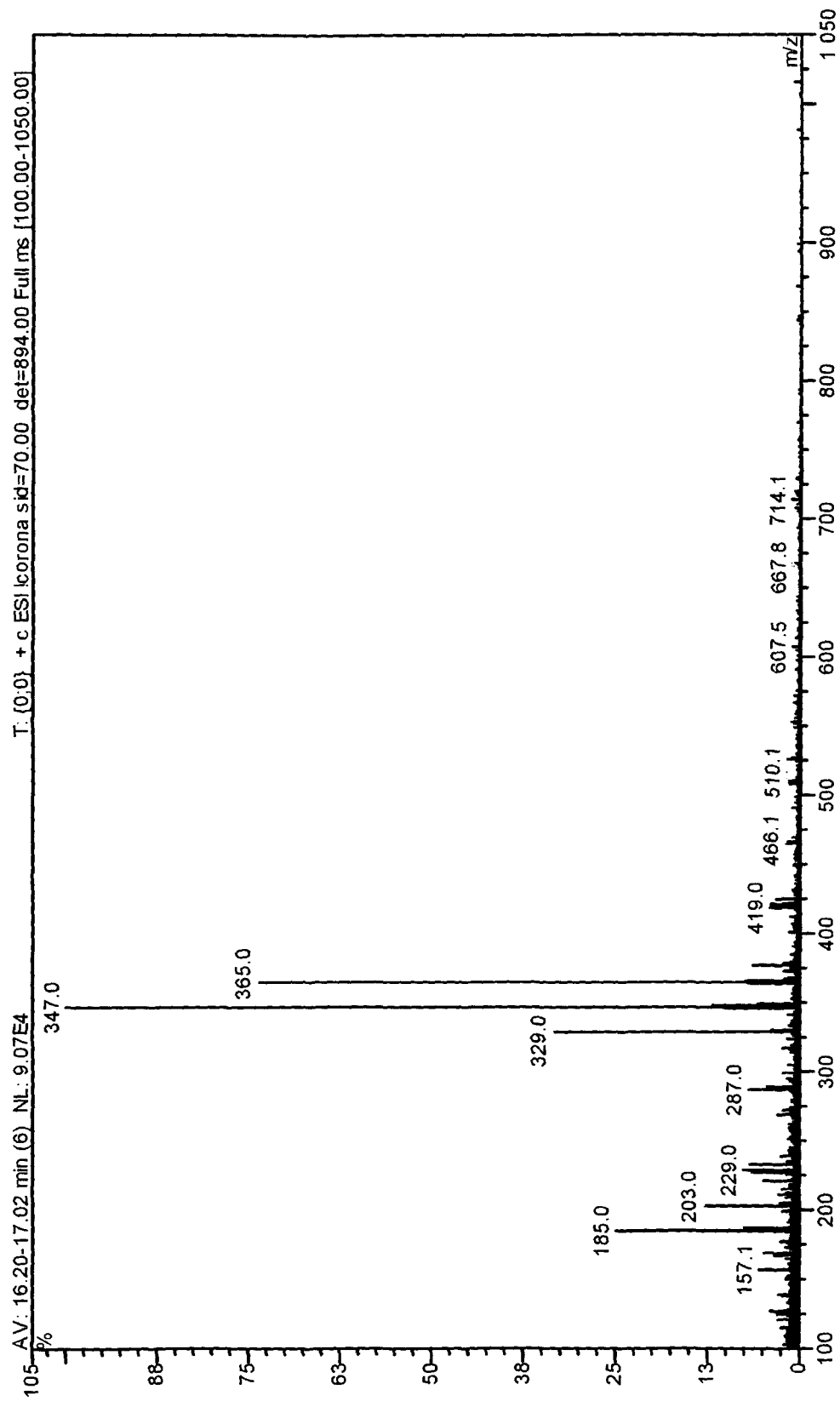
FIG. 6 is a full mass spectrum of the peak GlcGlc(C6-aldehyde)
Figure 7:
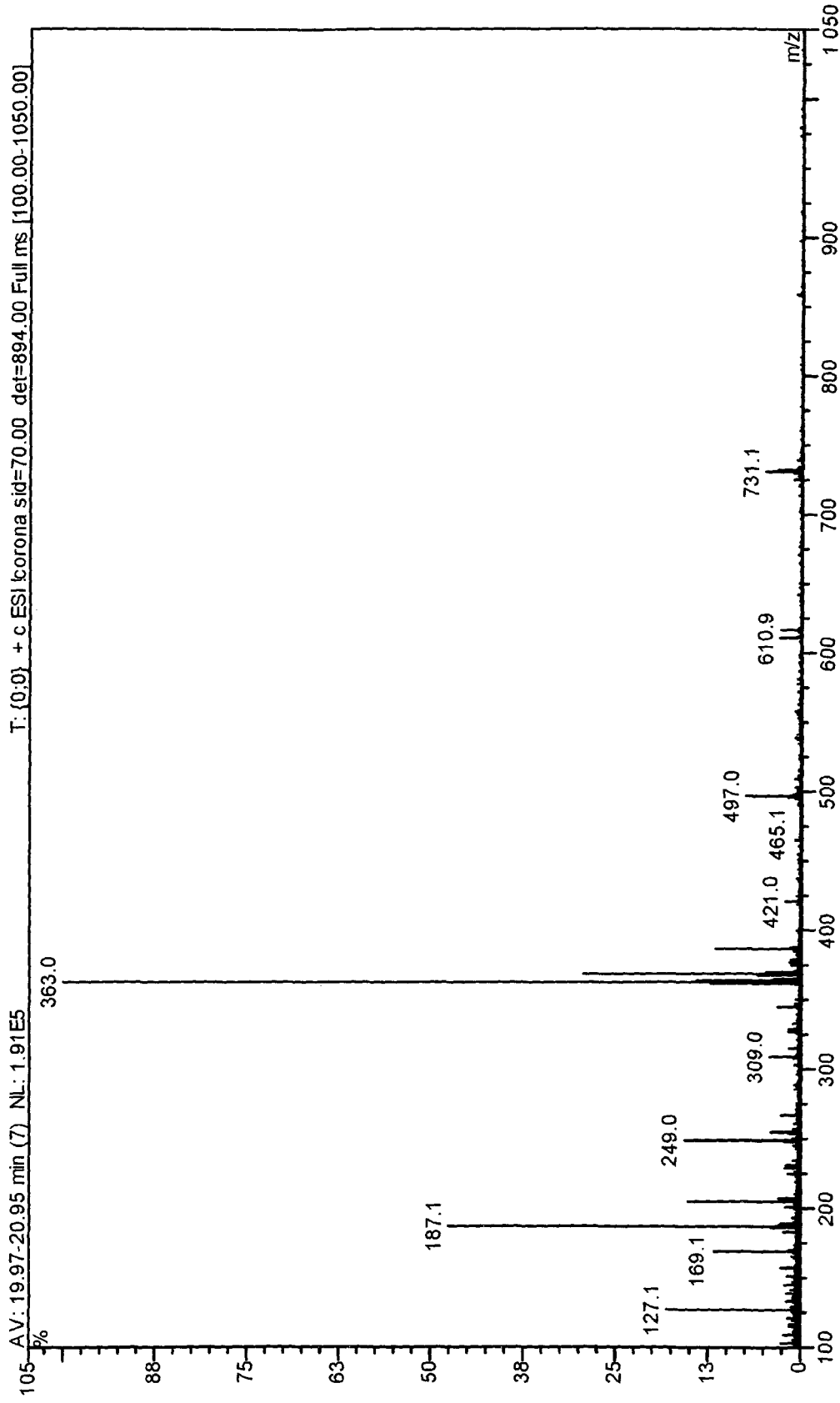
FIG. 7 is a full mass spectrum of the peak GlcGlcA.

Detected mass values for the dimers were 363, 365 and 347. Mass values of 365 and 347 (FIG. 6) relate to dimeric oligohexoses with aldehyde group attached i.e m/z at 347 is GlcGlc(C6 aldehyde) [M+Li] and m/z at 365 is same aldehyde including water as $[M+Li+H2O]$. The m/z 363 (FIG. 7) is dimeric oligohexose with acidic group attached on C6 carbon, GlcGlcA as [M+Li].

The dimeric oligohexoses, i.e. oxidized cellobioses GlcGlc(C6 aldehyde) and GlcGlcA are specific markers for oxidized nanofibrillar cellulose and they are not substantially found in pulp or paper.

Example 4. Quantification of the Oxidized Nanofibrillar Cellulose with the Standard Mixtures Standard mixtures, i.e. pulp samples containing defined concentrations of oxidized nanofibrillar cellulose, were prepared from a base pulp (softwood-hardwood, 30%/70%) and oxidized NFC grade A and grade B. First, oxidized nanofibrillar cellulose stock was diluted to 0.5% with distilled water and mixed with Bamix and under magnet stirring to have a smooth mixture. Defined amounts of oxidized nanofibrillar cellulose were weighed to the base pulp to end up to final concentrations of 0.5, 1.0, 2.0, 3.0 and 5% of oxidized nano-fibrillar cellulose in the mixture. Distilled water was added to set a final consistency of 4.0% (10 g dw) and mixed with Dispermat at ~1850 rpm for 10 min to obtain a homogenous sample. To ensure proper storage the standard mixtures were freeze-dried and stored in closed vials until used in the analysis.

Figure 8:
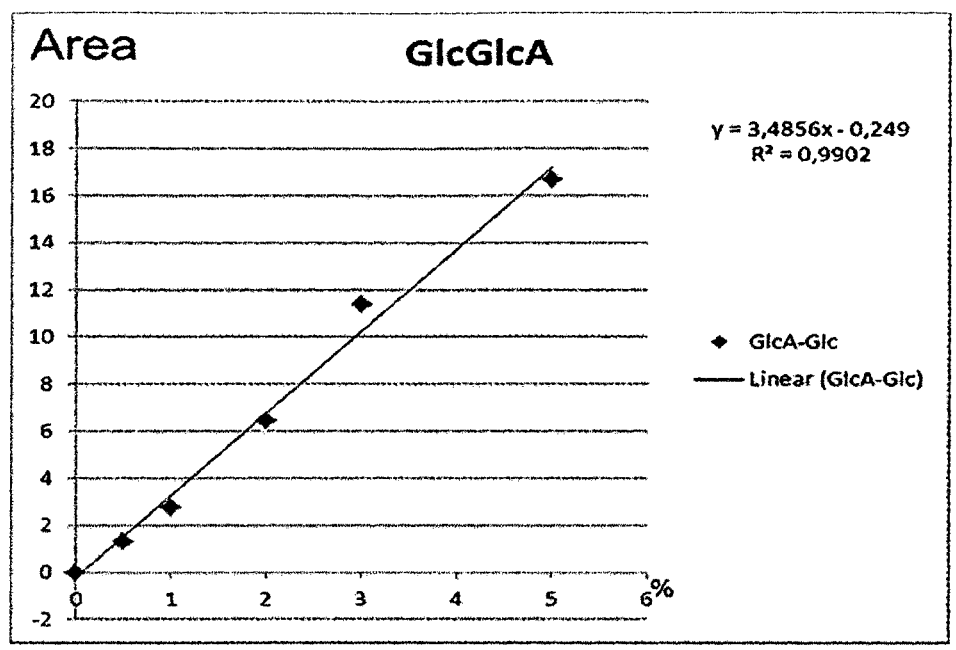
FIG. 8 is a standard curve for GlcGlcA obtained from the hydrolyzed standard mixtures containing oxidized nanofibrillar cellulose between 0% and 5%.

The dried standard mixtures were subjected to enzymatic hydrolysis as described in Example 2. The hydrolytes were diluted 1:1 in water, before the analysis by HPAEC-equipment. Quantification can be performed using either PAD detection or MSQ detector with selected mass values (SIM) of 363 and 347 (Example 3). The calibration curve was obtained by correlating peaks' area in the chromatogram to known amount of oxidized nanofibrillar cellulose in the standard mixtures. For example marker "GlcGlcA" area can be correlated to %—amount of oxidized nanofibrillar cellulose in the standard mixtures, since GlcGlcA does not naturally occur in pulps or paper products. Integration of these markers in mixtures gave a good linearity for prepared standards (FIG. 8). This calibration curve can be used to determine the amount of oxidized nanofibrillar cellulose in unknown paper products. In the analysis of unknown paper samples, standard mixtures need to be treated and hydrolyzed similarly as the samples.

Example 5. Analysis of Laboratory Sheets

Retention of oxidized nanofibrillar cellulose in pulp furnish during sheet forming was determined. Pulp furnish of softwood/hardwood (30%/70%) with defined amount of oxidized nanofibrillar cellulose grade (A and B), cationic starch and thereafter laboratory paper sheets were prepared according to the standard method described in Example 1. Small pieces of dried sheets, corresponding to about 100 mg dry weight, were cut into pieces with scissors, placed into a vial and hydrolyzed as described in Example 2. Standard mixtures carrying the known amount of oxidized nanofibrillar cellulose (e.g. 0.0, 0.5 and 1.0% w/w) were treated similarly. After hydrolysis concentration of dimeric oligohexoses, in particular oxidized cellobioses, in the test samples and standard mixtures were analyzed and quantified as described in Example 4. The results were as follows:

| Sample | Grade A dosage w/w % | Grade B dosage w/w % | Measured w/w % |
|---|---|---|---|
| 1 Ref | — | — | 0 |
| 2 | 0.5 | | 0.45 |
| 3 | 1.0 | | 0.95 |
| 4 | 2.0 | | 1.9 |
| 5 | | 0.5 | 0.4 |
| 6 | | 1.0 | 0.9 |
| 7 | | 2.0 | 1.6 |

Retention of oxidized nanofibrillar cellulose in laboratory paper sheets varied between 80 and 95% depending on the oxidized nanofibrillar cellulose grade used.

Example 6. Analysis of Paper Samples A (Wood-Free)

Filler containing wood free paper was produced on a (pilot) paper machine, according to Example 1. Oxidized nanofibrillar cellulose dosage amount was varied between 0.5 to 2% w/w.

| Sample | Grade B dosage w/w % | Grade B measured w/w % |
| --- | --- | --- |
| 1 ref | 0 | 0 |
| 2 | 0.5 | 0.4 |
| 3 | 1 | 0.4 |
| 4 | 2 | 0.45 |
| 5 | 2 | 0.65 |
| 6 | 1 | 0.45 |
| 7 | 1 | 0.6 |
| 8 post-run ref | 0 | 0.6 |

Retention of oxidized nanofibrillar cellulose in paper samples varied depending on retention systems and dosage position.

Example 7. Analysis of Paper Samples B (Wood Containing)

Filler containing LWC base paper was produced on a (pilot) paper machine, according to Example 1. Oxidized nanofibrillar cellulose dosage amount was varied between 1 to 3% w/w.

| Sample | Grade A dosage, cumulative % w/w | Grade A measured % w/w |
| --- | --- | --- |
| 1, ref. | 0 | — |
| 2 | 1 | 1.1 |
| 3 | 1 | 0.9 |
| 4 | 1.5 | 1.3 |
| 5 | 2.1 | 1.3 |
| 6 | 2.5 | 1.3 |
| 7 | 3 | 1.4 |
| 8 | 3 | 1.6 |

Retention of oxidized nanofibrillar cellulose in paper samples varied depending on retention systems and dosage position.

Example 8. Analysis of Paper Samples C (Wood Containing, Filler Containing)

Filler containing LWC base paper was produced on a paper machine, according to Example 1. Oxidized nanofibrillar cellulose dosage amount was varied between 1 to 3% w/w.

| Sample | Grade B dosage % w/w | Grade B measured % w/w |
| --- | --- | --- |
| 1, ref | 0 | 0 |
| 2 | 1 | 0.5 |
| 3 | 1.5 | 0.6 |
| 4 | 2 | 0.4 |
| 5 | 2 | 0.8 |
| 6 | 3 | 1.1 |
| 7, post run ref. | 0 | 0.2 |

Retention of oxidized nanofibrillar cellulose in paper samples varied depending on retention systems and dosage position.

Example 9. Analysis of Aqueous Samples

Concentration of oxidized nanofibrillar cellulose in an aqueous solution is determined. Aqueous solution sample is placed into a vial and hydrolyzed as described in Example 2. Oxidized nanofibrillar cellulose dosage amount is varied between 0.1 to 3% w/w. Standard mixtures carrying known amounts of oxidized nanofibrillar cellulose are treated similarly. After hydrolysis concentration of oxidized cellobioses in the test samples and standard mixtures is analyzed and quantified as described in Example 4.

It will be obvious to a person skilled in the art that, as the technology advances, the inventive concept can be implemented in various ways. The invention and its embodiments are not limited to the examples described above but may vary within the scope of the claims.

The invention claimed is:

1. A method for determining the concentration of oxidized nanofibrillar cellulose in an analytical sample, the method comprising:
   (a) providing an analytical sample of material comprising oxidized nanofibrillar cellulose;
   (b) hydrolyzing the analytical sample to breakdown products of the oxidized nanofibrillar cellulose in the presence of one or more enzymes, the breakdown products comprising monosaccharides and oxidized cellobiose;
   (c) subjecting the breakdown products to a separation analysis including analytical chromatography to separate the oxidized cellobiose and the monosaccharides to reveal the relative amounts of the breakdown products; and
   (d) determining the concentration of the oxidized nanofibrillar cellulose, wherein the concentration of the oxidized nanofibrillar cellulose is determined by comparing the relative amounts of the oxidized cellobiose in the analytical sample to at least two samples comprising different predetermined amounts of oxidized nanofibrillar cellulose.

2. The method as claimed in claim 1, wherein oxidized cellobiose is GlcA(b1-4)Glc, Glc(b1-4)GlcA, Glc(C6-aldehyde)(b1-4)Glc, and/or Glc(b1-4)Glc(C6-aldehyde).

3. The method as claimed in claim 1, wherein step (a) further comprises treating the material comprising oxidized nanofibrillar cellulose to obtain a homogenous analytical sample of the material comprising oxidized nanofibrillar cellulose, the treating including cutting, tearing, mixing, grinding, ball milling, sonication, refining, suspending in water, or any combination thereof.

4. The method as claimed in claim 1, wherein the one or more enzymes in step (b) are selected from the group consisting of cellulases and hemicellulases.

5. The method as claimed in claim 4, wherein the one or more enzymes in step (b) are selected from the group consisting of endoglucanases, cellobiohydrolases, xylanases, mannanases, β-D-glycosidases, β-D-xylosidases and β-D-mannosidases.

6. The method as claimed in claim 4, wherein the one or more enzymes of step (b) further comprises pectinases.

7. The method as claimed in claim 1, wherein the hydrolysis is carried out at a temperature ranging from 15 to 75° C.

8. The method as claimed in claim 1, wherein step (d) comprises determining an aldehyde and carboxylic acid ratio of the oxidized nanofibrillar cellulose.

9. The method as claimed in claim 8, wherein the aldehyde and carboxylic acid ratio is determined by comparing the relative amounts of GlcA(b1-4)Glc, Glc(b1-4)GlcA, Glc(C6-aldehyde)(b1-4)Glc, and/or Glc(b1-4)Glc(C6-aldehyde).

10. The method as claimed in claim 1, wherein in step (c) the separation analysis is analytical chromatography.

11. The method as claimed in claim 10, wherein analytical chromatography is high-performance liquid chromatography (HPLC) or high-performance anion exchange chromatography (HPAEC) coupled with a mass detector and/or pulsed amperometry detector (PAD).

12. The method as claimed in claim 10, wherein separation analysis is performed with HPAEC-PAD and a single quadrupole mass spectrometer (MSQ).

13. The method as claimed in claim 1, wherein the material comprising oxidized nanofibrillar cellulose is selected from the group consisting of paper, cardboard, pulp, pulping liquor, and cellulose based nonwovens.

14. The method as claimed in claim 1, wherein the material comprising oxidized nanofibrillar cellulose is an aqueous solution.

15. The method of claim 1, wherein the hydrolysis is carried out at a temperature ranging from room temperature to about 50° C.

16. The method of claim 1, wherein the hydrolysis is carried out at a temperature ranging from about 35° C. to about 45° C.

* * * * *

UNITED STATES PATENT AND TRADEMARK OFFICE
CERTIFICATE OF CORRECTION

PATENT NO. : 10,520,485 B2
APPLICATION NO. : 14/783735
DATED : December 31, 2019
INVENTOR(S) : Antti Laukkanen et al.

Page 1 of 1

It is certified that error appears in the above-identified patent and that said Letters Patent is hereby corrected as shown below:

In the Claims

At Column 12, Lines 56-57 (Claim 4, Lines 2-3), please delete "are selected from the group consisting of" and insert --comprises-- therefor.

Signed and Sealed this
Third Day of March, 2020

Andrei Iancu
*Director of the United States Patent and Trademark Office*